United States Patent [19]

Ekeze et al.

[11] Patent Number: 5,622,822
[45] Date of Patent: Apr. 22, 1997

[54] METHODS FOR CAPTURE AND SELECTIVE RELEASE OF NUCLEIC ACIDS USING POLYETHYLENEIMINE AND AN ANIONIC PHOSPHATE ESTER SURFACTANT AND AMPLIFICATION OF SAME

[75] Inventors: Tobias E. Ekeze, Rocheser; John W. Backus, Williamson; David J. Sharkey, Rochester; Richard C. Sutton, Rocheser; JoAnne H. Kerschner, Rochester, all of N.Y.

[73] Assignee: Johnson & Johnson Clinical Diagnostics, Inc., Rochester, N.Y.

[21] Appl. No.: 305,769

[22] Filed: Sep. 13, 1994

[51] Int. Cl.⁶ .............................. C12Q 1/68; C12Q 1/70; C12P 19/34; C07H 21/04
[52] U.S. Cl. .................. 435/6; 435/5; 435/91.2; 435/91.1; 536/24.3; 536/24.32; 536/24.33; 424/94.1
[58] Field of Search ................... 435/6, 5, 91.2; 536/24.3–24.33; 424/94.1

[56] References Cited

U.S. PATENT DOCUMENTS

| | | | |
|---|---|---|---|
| 3,176,006 | 3/1965 | Zahn | 260/211.5 |
| 4,693,980 | 9/1987 | Stetter et al. | 435/199 |
| 5,092,992 | 3/1992 | Crane et al. | 210/198.2 |
| 5,141,857 | 8/1992 | DiFrancesco | 435/91 |
| 5,354,843 | 10/1994 | Rink et al. | 530/307 |
| 5,473,060 | 12/1995 | Gryaznov et al. | 536/24.3 |

FOREIGN PATENT DOCUMENTS

| | | | |
|---|---|---|---|
| 507591 | 4/1991 | European Pat. Off. | G01N 30/34 |
| 1298431 | 12/1974 | United Kingdom . | |
| 1411503 | 10/1975 | United Kingdom | C07G 7/028 |

OTHER PUBLICATIONS

Hoopes and McClure, NAR 9: 5493–5504. 1981.
Scopes, In PRotein Purification: PRinciples and Practice, Springer Verlag, pp. 100–114. 1987.
Renz et al, Nucl Acids Res., 12, pp. 3435–3444, 1984.

*Primary Examiner*—Stephanie W. Zitomer
*Assistant Examiner*—Dianne Rees

[57] ABSTRACT

Nucleic acids can be made available for amplification or other treatment after lysis by contacting the lysate with polyethyleneimine to form a precipitate with the nucleic acids. The nucleic acids are then released from the precipitate by contact with a strong base, and the released nucleic acids are kept in solution with an anionic phosphate ester surfactant. This method for preparing specimen samples is simple and quite rapid.

18 Claims, 4 Drawing Sheets

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 27 nucleotides
        ( B ) TYPE: nucleic acid
        ( C ) STRANDEDNESS: single
        ( D ) TOPOLOGY: linear     ( i i ) MOLECULE TYPE: Primer for hCMV DNA     ( i i i ) HYPOTHETICAL: NO     ( i v ) ANTI-SENSE: NO     ( v i ) ORIGINAL SOURCE: Synthetically prepared     ( v i i ) IMMEDIATE SOURCE: Synthetically prepared     ( x ) PUBLICATION INFORMATION: Unknown     ( x i ) SEQUENCE DESCRIPTION: SEQ ID NO:1:

CATTCCCACT GACTTTCTGA CGCACGT     27

( 2 ) INFORMATION FOR SEQ ID NO:2:

( i ) SEQUENCE CHARACTERISTICS:
        ( A ) LENGTH: 24 nucleotides
        ( B ) TYPE: nucleic acid
        ( C ) STRANDEDNESS: single
        ( D ) TOPOLOGY: linear     ( i i ) MOLECULE TYPE: Primer for hCMV DNA     ( i i i ) HYPOTHETICAL: NO     ( i v ) ANTI-SENSE: NO     ( v i ) ORIGINAL SOURCE: Synthetically prepared     ( v i i ) IMMEDIATE SOURCE: Synthetically prepared     ( x ) PUBLICATION INFORMATION: None     ( x i ) SEQUENCE DESCRIPTION: SEQ ID NO:2:

TGAGGTCGTG GAACTTGATG GCGT     24

( 2 ) INFORMATION FOR SEQ ID NO:3:

( i ) SEQUENCE CHARACTERISTICS:
        ( A ) LENGTH: 30 nucleotides
        ( B ) TYPE: nucleic acid
        ( C ) STRANDEDNESS: single
        ( D ) TOPOLOGY: linear     ( i i ) MOLECULE TYPE: Capture probe of hCMV DNA     ( i i i ) HYPOTHETICAL: NO     ( i v ) ANTI-SENSE: NO     ( v i ) ORIGINAL SOURCE: Synthetically prepared     ( v i i ) IMMEDIATE SOURCE: Synthetically prepared ( x ) PUBLICATION INFORMATION: Unknown ( x i ) SEQUENCE DESCRIPTION: SEQ ID NO:3:

GGTCATCGCC GTAGTAGATG CGTAAGGCCT 30

METHODS FOR CAPTURE AND SELECTIVE RELEASE OF NUCLEIC ACIDS USING POLYETHYLENEIMINE AND AN ANIONIC PHOSPHATE ESTER SURFACTANT AND AMPLIFICATION OF SAME

FIELD OF THE INVENTION

This invention relates to a method for preparing a sample by capture and selective release of nucleic acids for detection. In particular, it relates to a method for capture and release of nucleic acids for subsequent treatment such as amplification. It also relates to a test kit for use in the method.

BACKGROUND OF THE INVENTION

Technology to detect minute quantities of nucleic acids has advanced rapidly over the last two decades including the development of highly sophisticated amplification techniques such as polymerase chain reaction (PCR) and ligase chain reaction (LCR). Researchers have readily recognized the value of such technology to detect diseases and genetic features in human or animal test specimens. The use of probes and primers in such technology is based upon the concept of complementarity, that is, the bonding of two strands of a nucleic acid by hydrogen bonds between complementary nucleotides (also known as nucleotide pairs).

PCR is a significant advance in the art to allow detection of very small concentrations of a targeted nucleic acid. The details of PCR are described, for example, in U.S. Pat. No. 4,683,195 (Mullis et al), U.S. Pat. No. 4,683,202 (Mullis) and U.S. Pat. No. 4,965,188 (Mullis et al), although there is a rapidly expanding volume of literature in this field.

In order to effectively amplify and detect a target nucleic acid, it is usually necessary to isolate that nucleic acid from cellular and other specimen debris. Various lysing procedures are known, including freezing, treatment with digesting enzyme such as proteases (for example, Proteinase K), boiling, use of various detergents (see for example U.S. Ser. No. 178,202, filed Apr. 6, 1988 by Higuchi, and EP-A-0 428 197, published May 22, 1991), solvent precipitations and heating protocols.

Once nucleic acids are extracted, however, there sometime remains a need to separate them from other materials in the lysate due to the presence of inhibitors or interferents in the lysate. One material known to complex with nucleic acids is polyethyleneimine. It has been used to precipitate nucleic acids as contaminants in processes for isolating enzymes such as Q Beta replicase (see U.S. Pat. No. 5,141,857 of DiFrancesco). Affinity columns containing derivatives of polyethyleneimine have also been prepared for capturing nucleic acids, as described for example in U.S. Pat. No. 5,092,992 (Crane et al).

The mere use of polyethyleneimine to precipitate nucleic acids is insufficient to provide target analytes useful for further treatment. The precipitate cannot be used in that form, and release of the nucleic acids from the precipitate is difficult to achieve. Moreover, the nucleic acids which are bound to the polyethyleneimine cannot be amplified using conventional amplification techniques. Thus, a series of problems arise in the selective capture and release of target nucleic acids for subsequent treatment, and no ready solution to those problems is suggested by known procedures.

There remains a need, therefore, for an efficient and simple means for preparing nucleic acids in a sample for amplification or other hybridization procedures.

SUMMARY OF THE INVENTION

The problems noted above are overcome with a method for providing a nucleic acid from a lysate comprising the steps of:

A) contacting a lysate suspected of containing a nucleic acid with polyethyleneimine in an amount sufficient to form a water-insoluble precipitate of polyethyleneimine with all nucleic acids present in the lysate, B) separating the water-insoluble precipitate from the lysate, C) contacting the separated water-insoluble precipitate with a strong base to release the nucleic acids from the polyethyleneimine, and D) simultaneously with or subsequently to step C), contacting the nucleic acids with an anionic phosphate ester surfactant to keep the released nucleic acids in solution.

This invention also provides a method having steps A) through D) described above, taken in addition with step:

E) adjusting the pH of the solution containing the released nucleic acids to from about 6 to about 9.

This invention also provides a method for the amplification and detection of a target nucleic acid comprising:

I) providing a target nucleic acid from a lysate using the steps of:
   A) contacting a lysate suspected of containing a nucleic acid with polyethyleneimine in an amount sufficient to form a water-insoluble precipitate of polyethyleneimine with all nucleic acids present in the lysate, including a target nucleic acid,
   B) separating the water-insoluble precipitate from the lysate,
   C) contacting the separated water-insoluble precipitate with a strong base to release the nucleic acids from the polyethyleneimine,
   D) simultaneously with or subsequently to step C), contacting the released nucleic acids with an anionic phosphate ester surfactant to keep the released nucleic acids in solution, and
   E) adjusting the pH of the solution containing the released nucleic acids to from about 6 to about 9, II) amplifying the target nucleic acid among the released nucleic acids, and III) detecting the amplified target nucleic acid.

Further, a test kit for amplification of a target nucleic acid comprises, separately packaged:

a) an amplification reaction mixture comprising one or more amplification reagents, b) polyethyleneimine, and c) an anionic phosphate ester surfactant.

The present invention provides a rapid, simple and effective method for selectively isolating and providing nucleic acids for further treatment, such as hybridization assays or amplification procedures. This invention overcomes the problems noted above relating to conventional use of polyethyleneimine by providing a means for releasing captured nucleic acids from polyethyleneimine and keeping the nucleic acids dispersed so they do not recomplex with the polyethyleneimine. The sample preparation method of this invention is not tedious and requires a minimum of steps. It usually can be carried out within 15 minutes (preferably within 10 minutes). It avoids organic solvents used in conventional procedures and utilizes relatively inexpensive reagents.

While the polyethyleneimine performs a useful function to capture nucleic acids in a specimen, the nucleic acids cannot be used when complexed with polyethyleneimine. Thus, the precipitate of nucleic acid and polyethyleneimine is contacted with a strong base to release the nucleic acids. To keep the released nucleic acids dispersed in solution, they are contacted with a select class of surfactants, namely anionic phosphate esters, while at high pH. Generally, the pH then must be lowered so the nucleic acids can be used in some manner. The surfactant maintains the nucleic acids in solution even at the lowered pH.

DETAILED DESCRIPTION OF THE INVENTION

The present invention is especially suited for the extraction and detection of one or more target nucleic acids present in a specimen sample of any type collected from plants, animals, humans or the environment. The nucleic acids so obtained can be further detected by subjecting them to conventional hybridization assays, the procedures of which are well known in the art (for example, U.S. Pat. No. 4,994,373, incorporated herein by reference with respect to the hybridization technology).

However, for the sake of brevity, the remaining discussion will be directed to preferred embodiments whereby the nucleic acids are subjected to amplification procedures, particularly PCR. However, the scope of this invention is not intended to be so limited because other amplification techniques (such as LCR) can be used also.

The general principles and conditions for amplification and detection of nucleic acids using polymerase chain reaction are quite well known, the details of which are provided in numerous references including U.S. Pat. No. 4,683,195 (Mullis et al), U.S. Pat. No. 4,683,202 (Mullis), U.S. Pat. No. 4,965,188 (Mullis et al) and WO-A-91/12342. The noted U.S. patents are incorporated herein by reference. In view of the teaching in the art and the specific teaching provided herein, a worker skilled in the art should have no difficulty in practicing the present invention by combining the sample preparatory method of this invention with polymerase chain reaction procedures.

Other amplification procedures which can be used in the practice of this invention include ligase chain reaction as described, for example, in EP-A-0 320 308 (published December, 1987) and EP-A-0 439 182 (published January, 1990).

Test specimens can include cellular or viral material, hair, body fluids or other materials containing nucleic acids. The target nucleic acid can be extracted from any suitable human, animal, cellular culture, microbial, viral, plant or environmental source.

Bacteria which can be detected include, but are not limited to, bacteria which may be found in blood, *Salmonella spp.*, *Strepococcus spp.*, *Chlamydia spp.*, *Neisseria spp.*, *Mycobacterium spp.* (such as *Mycobacterium tuberculosis* and *Mycobacterium avium* complex), *Mycoplasma spp.* (such as *Mycoplasma pneumoniae*), *Legionella pneumophila*, *Borrelia burgdorferei*, *Pneumocystis carinii*, *Clostridium difficile*, *Campylobacter spp.*, *Yersinia spp.*, *Shigella spp.* and *Listeria monocytogenes*. Viruses which are detectable include, but are not limited to, herpes simplex viruses, Epstein Barr virus, cytomegalovirus, human papilloma viruses, influenza viruses, respiratory syncytial virus, hepatitis viruses and retroviruses (such as HTLV-I, HTLV-II, HIV1 and HIV2). Protozoan parasites and fungi (including yeasts and molds) are also detectable. Other detectable species would be readily apparent to one skilled in the art. The invention is particularly useful for the detection of the presence of nucleic acids associated with various bacteria or viruses.

In a preferred embodiment, the invention is useful for the isolation, amplification and detection of nucleic acids associated with HIV1, HIV2, proviral HIV1, proviral HIV2, cytomegalovirus, human papilloma virus, *Mycobacterium spp.*, hepatitis viruses or human genetic diseases.

Prior to contact with polyethyleneimine, nucleic acids can be extracted from the specimen in any suitable manner. Various lysing procedures are known in the art, including those described by Laure et al in *The Lancet*, pp. 538–540 (Sep. 3, 1988), Maniatis et al, *Molecular Cloning: A Laboratory Manual*, pp. 280–281 (1982), Gross-Belland et al in *Eur. J. Biochem.*, 36, 32 (1973) and U.S. Pat. No. 4,965,188 (noted above). Extraction of DNA from whole blood or components thereof are described, for example, in EP-A-0 393 744 (published Oct. 24, 1990) and U.S. Pat. No. 5,231,015 (Cummins et al), the Cummins et al patent being incorporated herein by reference.

While the particular lysing procedure is not critical to the practice of this invention, a preferred lysing procedure includes heating the specimen in the presence of a suitable nonionic surfactant, a number of which are well known in the art. A representative lysing procedure is described in Example 5 below.

The lysate is then mixed with polyethyleneimine to provide at least 0.005 final weight percent. Polyethyleneimine can be obtained from a number of commercial sources. This amount is usually sufficient to form a water-insoluble precipitate with all of the nucleic acids present in the lysate thereby precipitating the nucleic acids from the lysate. Of course, a skilled artisan would know how to adjust the amount of polyethyleneimine to accommodate any quantity of nucleic acids. Preferably, the final solution concentration of polyethyleneimine is from about 0.01 to about 1 weight percent. Mixing can be carried out in any suitable manner for up to 30 minutes and at any suitable temperature (generally from 15° to 35° C.).

The precipitate can be removed from the lysate, if desired, prior to mixing with a strong base in order to remove inhibitors or interferents, or cellular debris, or to concentrate the nucleic acids. For example, the lysate containing the precipitate can be centrifuged and the supernatant discarded.

The captured nucleic acids are released (or decomplexed) from the water-insoluble precipitate by contacting the precipitate with a strong base. By strong base is meant a base which is able to raise solution pH to at least 10 (preferably, at least 11). Such bases include, but are not limited to, sodium hydroxide, potassium hydroxide, lithium hydroxide, ammonium hydroxide and any other organic or inorganic base which would be readily apparent to one skilled in the art. The amount of strong base to be used would be readily apparent to a skilled worker in the art depending upon the strength of the base and the volume of solution. Sodium hydroxide is preferred in the practice of this invention.

Mixing with the strong base can be carried out using any suitable mixing means, for a suitable time (generally at least 1 minute) and at a suitable temperature (generally from about 15° to about 35° C.) which would be readily apparent to one skilled in the art. The resulting mixture is generally at a pH greater than or equal to 11.

One or more surfactants of a specific class of compounds are used to keep the nucleic acids in solution. This surfactant can be mixed with the precipitate simultaneously with adding the strong base, but preferably, the surfactant is added after the strong base has had time to effect release of nucleic acids.

The useful surfactants are water-soluble, anionic, nonaromatic phosphate esters. Such materials can be obtained from several commercial sources, including DuPont under the trademark ZONYL™ FSP, and Witco Corp. under the trademark EMPHOS™. The materials available as ZONYL™ FSP and EMPHOS™ PS413 anionic surfactants are representative with the first one being preferred.

More specifically, the useful surfactants are nonaromatic, fluorinated phosphate esters or nonaromatic, nonfluorinated oxyalkylatedalkyl phosphate esters (including mono- and diesters), and equivalent salts.

Generally, nonaromatic fluorinated phosphate esters have at least one perfluoroaliphatic group (that is, a $C_nF_{2n+1}$ group), and preferably, most of the aliphatic groups in the molecule are perfluorinated, such as in ZONYL™ FSP anionic surfactant. A more general structure of some of these compounds is wherein $R_f$ is a fluoroaliphatic radical having up to 10 carbon atoms, Q is a multivalent linking group, such as alkylene, sulfonamidoalkylene, carbonamidoalkylene and equivalent hydrocarbon groups, with up to 10 carbon and heteroatoms in the chain, Z is phosphate, $M^+$ is an alkali metal (such as sodium or potassium) or ammonium cation, m is 1 or 2, n is 1 or 2, and a is 0 or 1. M can be other monovalent cations which would be readily apparent to one skilled in the art.

The esters can be used in the form of alkali metal, ammonium or alkylammonium salts.

A preferred anionic fluorinated phosphate ester useful in this invention is Zonyl™ FSP anionic surfactant which has the structure:

wherein M is a cation as defined above.

The final solution concentration of anionic perfluorinated phosphate ester used at this point is generally at least about 0.05 weight percent, with from about 0.1 to about 1.5 weight percent being preferred. The amount may vary with a given surfactant and the amount of polyethyleneimine and nucleic acids which are present in the resulting solution. Some surfactants may work best at concentrations at which other surfactants are ineffective. The surfactant has been found to keep the nucleic acids from recomplexing with the polyethyleneimine and thereby keep them available for further treatment at lowered pH. The amount of nucleic acids released and solubilized in this manner will depend, of course, on the concentration of nucleic acids and polyethyleneimine present, the amount of surfactant used and the time and temperature of mixing. If the target nucleic acid is believed to be present in very low amounts, a skilled worker would consider this factor in choosing the various conditions of mixing and amounts of reagents.

Mixing of the released nucleic acids and surfactant can be carried out for a suitable time (generally at least 1 minute) and at a suitable temperature (generally from about 15° to about 35° C.) which would be readily apparent to one skilled in the art.

The resulting solution containing released nucleic acids has a high pH, so generally its pH is adjusted for further treatment, such as efficient amplification or hybridization assays. Adjustment of pH is typically accomplished by mixing the solution with a suitable amount of a suitable buffer, such as tris(hydroxymethyl)aminomethane hydrochloride, and others which would be readily apparent to one skilled in the art. The pH of the final mixture is generally in the range of from about 6 to about 9.

This step can be carried out immediately, or it can be delayed until a later time with the released nucleic acids stored at high pH.

The described methods of this invention for capturing and releasing nucleic acids of this invention is typically carried out within about 15 minutes, and preferably within about 10 minutes.

As used herein in defining amounts and time (unless otherwise noted), the modifier "about" refers to a variance of ±10% of the noted values. In defining pH, "about" refers to ±0.5 pH unit.

The present invention is also directed to the amplification or detection of one or more specific nucleic acid sequences present in one or more target nucleic acids which are captured and released using the method described above. Moreover, a plurality of target nucleic acids can be amplified and detected simultaneously by using a corresponding set of primers and detection means for each specific nucleic acid. Multiple sequences in the same nucleic acid can also be amplified and detected.

A "PCR reagent" refers to any of the reagents considered essential to PCR, namely a set of primers for each target nucleic acid, a DNA polymerase, a DNA polymerase cofactor and two or more deoxyribonucleoside-5'-triphosphates (dNTP's).

As used herein in referring to primers or probes, the term "oligonucleotide" refers to a molecule comprised of four or more deoxyribonucleotides or ribonucleotides, and preferably more than ten. Its exact size is not critical but depends upon many factors including the ultimate use or function of the oligonucleotide. The oligonucleotide may be derived by any method known in the art.

The term "primer" refers to an oligonucleotide, whether naturally occurring or synthetically produced, which is capable of acting as a point of initiation of synthesis when placed under conditions in which synthesis of a primer extension product complementary to a nucleic acid strand (that is, template) is induced. Such conditions include the presence of nucleotides (such as the four standard deoxyribonucleoside-5'-triphosphates), a DNA polymerase and a DNA polymerase cofactor, and suitable temperature and pH. Normally, such conditions are what are known in the art as "high stringency" conditions so that nonspecific amplification is minimized. The primer must be long enough to initiate the synthesis of extension products in the presence of the DNA polymerase. The exact size of each primer will vary depending upon the use contemplated, the complexity of the targeted sequence, reaction temperature and the source of the primer. Generally, the primers used in this invention will have from 10 to 60 nucleotides.

Primers useful herein can be obtained from a number of sources or prepared using known techniques and equipment, including for example, an ABI DNA Synthesizer (available from Applied Biosystems) or a Biosearch 8600 Series or 8800 Series Synthesizer (available from Milligen-Biosearch, Inc.) and known methods for their use (for example as described in U.S. Pat. No. 4,965,188). Naturally occurring primers isolated from biological sources are also useful (such as restriction endonuclease digests). As used herein, the term "primer" also refers to a mixture of primers. Thus, each set of primers for a given target nucleic acid may include two or more primers for each opposing target strand.

One or both primers can be labeled with the same or different label for detection or capture of amplified product. Procedures for attaching labels and preparing primers are well known in the art, for example, as described by Agrawal et al, *Nucleic Acid Res.*, 14, pp. 6227–45 (1986), U.S. Pat. No. 4,914,210 (Levenson et al) relating to biotin labels, U.S. Pat. No. 4,962,029 (Levenson et al) relating to enzyme labels, and the references noted therein. Useful labels also include radioisotopes, electron-dense reagents, chromogens, fluorogens, phosphorescent moieties, ferritin and other magnetic particles (see U.S. Pat. No. 4,795,698 of Owen et al and U.S. Pat. No. 4,920,061 of Poynton et al), chemiluminescent moieties (such as luminol), and other specific binding species (avidin, streptavidin, biotin, sugars or lectins). Preferred labels are enzymes, radioisotopes and specific binding species (such as biotin). Useful enzymes include, glucose oxidase, peroxidases, uricase, alkaline phosphatase and others known in the art and can be attached to oligonucleotides using known procedures. Reagents to provide a colorimetric or chemiluminescent signal with such enzymes are well known.

Where the label is an enzyme such as a peroxidase, at some point in the assay, hydrogen peroxide and suitable dye-forming compositions are added to provide a detectable dye. For example, useful dye-providing reagents include tetramethylbenzidine and derivatives thereof, and leuco dyes, such as water-insoluble triarylimidazole leuco dyes (as described in U.S. Pat. No. 4,089,747 of Bruschi), or other compounds which react to provide a dye in the presence of peroxidase and hydrogen peroxide. Particularly useful dye-providing compositions are described in EP-A-0 308 236 (published Mar. 22, 1989). Chemiluminescent signals in response to a peroxidase label can also be generated using the appropriate reagents.

If one or both primers are biotinylated, the amplified nucleic acid can be detected using detectably labeled avidin or an equivalent thereof (such as streptavidin). For example, avidin can be conjugated with an enzyme, or have a radioisotope using known technology. Biotin on the amplified product complexes with the avidin, and appropriate detection techniques to detect a radioactive, colorimetric or chemiluminescent signal are used.

As used herein, a capture "probe" is an oligonucleotide which is substantially complementary to a nucleic acid sequence of one or more strands of the target nucleic acid, and which is used to insolubilize the amplified nucleic acid. The probe oligonucleotide is generally attached to a suitable water-insoluble substrate such as polymeric or glass beads, microtiter plate well, thin polymeric or cellulosic film or other materials readily apparent to one skilled in the art. The oligonucleotide is generally from about 12 to about 40 nucleotides in length, although the length is not critical.

A DNA polymerase is an enzyme which will add deoxynucleoside monophosphate molecules to the 3'-hydroxy end of the primer in a complex of primer and template, but this addition is in a template dependent manner (that is, dependent upon the specific nucleotides in the template). Many useful DNA polymerases are known in the art. Preferably, the polymerase is "thermostable", meaning that it is stable to heat, especially the high temperatures used for denaturation of DNA strands. More particularly, the thermostable DNA polymerases are not substantially inactivated by the high temperatures used in PCR as described herein.

A number of thermostable DNA polymerases have been reported in the art, including those mentioned in detail in U.S. Pat. No. 4,965,188 (noted above) and U.S. Pat. No. 4,889,818 (Gelfand et al), incorporated herein by reference. Particularly useful polymerases are those obtained from various Thermus bacterial species, such as *Thermus aquaticus, Thermus thermophilus, Thermus filiformis* or *Thermus flavus*. Other useful thermostable polymerases are obtained from a variety of other microbial sources including *Thermococcus literalis, Pyrococcus furiosus, Thermotoga sp.* and those described in WO-A-89/06691 (published Jul. 27, 1989). Some useful polymerases are commercially available. A number of techniques are known for isolating naturally-occurring polymerases from organisms, and for producing genetically engineered enzymes using recombinant techniques, as noted in the art cited in this paragraph.

A DNA polymerase cofactor refers to a nonprotein compound on which the enzyme depends for activity. A number of such materials are known cofactors including manganese and magnesium salts. Useful cofactors include, but are not limited to, manganese and magnesium chlorides, sulfates, acetates and fatty acid salts (for example, butyric, caproic, caprylic, capric and lauric acid salts). The smaller salts, that is chlorides, sulfates and acetates, are preferred.

Also needed for PCR are two or more deoxyribonucleoside-5'-triphosphates, such as dATP, dCTP, dGTP, dUTP or dTTP. Usually, dATP, dCTP, dGTP and dTTP are all used in PCR. Analogues such as dITP and 7-deaza-dGTP are also useful.

Also useful in the practice of the invention is an antibody specific to the DNA polymerase, which antibody inhibits its enzymatic activity at temperatures below about 50° C., but which antibody is deactivated at higher temperatures. Representative monoclonal antibodies having these properties are described in U.S. Pat. No. 5,338,671 (Scalice et al), incorporated herein by reference. Antibody fragments can be used in place of the whole molecule if they have equivalent properties.

The PCR reagents described herein are provided and used in PCR in suitable concentrations to provide amplification of the target nucleic acid. The minimal amounts of DNA polymerase is generally at least about 1 unit/100 μl of solution, with from about 4 to about 25 units/100 μl being preferred. A "unit" is defined herein as the amount of enzyme activity required to incorporate 10 nmoles of total nucleotides (dNTP's) into an extending nucleic acid chain in 30 minutes at 74° C. The concentration of each primer is at least about 0.075 μmolar with from about 0.2 to about 1 μmolar being preferred. In most instances, all primers are present in about the same amount (within a variation of 10% of each). However, in other instances, the amounts of individual primers may be manipulated to achieve most efficiency coamplification of multiple targets. The cofactor is generally present in an amount of from about 1 to about 15 mmolar, and each dNTP is generally present at from about 0.1 to about 3.5 mmolar in the reaction mixture. As used in this paragraph, the modifier "about" refers to a a variance of ±10% of the noted value.

The PCR reagents can be supplied individually, or in a buffered solution having a pH in the range of from about 7 to about 9 using any suitable buffer.

Since the target nucleic acid to be amplified and detected is usually in double strand form, the two strands must be separated (that is, denatured) before priming can take place. This can occur during the extraction process, but preferably, it occurs in a separate step afterwards. Heating to a suitable temperature (identified as "first temperature" or $T_1$ herein) is a preferred means for denaturation. Generally, this first temperature is in the range of from about 85° to about 100° C. for a suitable time, for example from 1 to about 240 seconds (preferably 1 to about 40 seconds). This initial denaturation step can also be included in the first amplification cycle. In such instances, denaturation may be longer in the first cycle (for example, up to 240 seconds) whereas later cycles can have much shorter denaturation steps (for example, up to 30 seconds).

The denatured strands are then primed with the appropriate primers by cooling the reaction mixture to a second temperature, $T_2$, which is generally within the range of from about 55° to about 75° C. It is desired that cooling is done quickly as possible, but with presently known equipment, it generally takes place over a time period of from about 5 to about 40 seconds, and more preferably for from about 5 to about 20 seconds.

Once the denatured strands are cooled, the reaction mixture containing the PCR reagents is incubated at a third temperature, $T_3$, generally for from 1 to about 120 seconds, and preferably for from 1 to about 80 seconds, to effect formation of primer extension products. Generally, the third temperature is generally within the range of from about 55 to about 75° C. Preferably, it is within the range of from about 62° to about 70° C.

In a most preferred embodiment, the second and third temperatures are the same and are within the range of from about 62° to about 70° C. Thus, priming and primer extension are preferably carried out in the same step.

Thus, an amplification cycle comprises the denaturation, priming (or annealing) and primer extension steps described above. Generally, at least 15 of such amplification cycles are carried out in the practice of this invention with the maximum number of cycles being within the discretion of the particular user. In most instances, 15 to 50 amplification cycles are used in the method with 15 to 40 cycles being preferred. Each amplification cycle is generally from about 20 to about 360 seconds, with a cycle time of from about 30 to about 120 seconds being preferred and from about 30 to about 90 seconds being more preferred. However, longer or shorter cycle times can be used if desired.

When used in reference to time for a given step in the amplification procedure, the term "about" refers to ±10% of that time limit. Moreover, when used in reference to temperatures, the term "about" refers to ±5° C.

The amplification method of this invention is preferably conducted in a continuous, automated manner so that the reaction mixture is temperature cycled in a controlled manner for a desired number of times. A number of instruments have been developed for this purpose, as one of ordinary skill in the art would know. Preferably, the instrument used will also be programmable for any type of amplification cycle desired.

One such instrument for this purpose is described in some detail in U.S. Pat. No. 4,965,188 and EP-A-0 236,069. Generally, this instrument includes a heat conducting container for holding a number of reaction tubes containing reaction mixture, a means for heating, cooling and temperature maintenance, and a computing means to generate signals to control the amplification sequence, changes in temperature and timing.

EP-A-0 402 994 provides details of useful chemical test packs which can be processed using the instrument described in U.S. Pat. No. 5,089,233 (Devaney, Jr. et al), incorporated herein by reference. Also described therein are means for heating and cooling the test pack at repeated intervals (that is, through cycles) appropriate for the method of the present invention. Further details regarding useful PCR processing equipment can be obtained from the considerable literature in the field, and would be readily known by one skilled in the art.

Besides chemical test packs described above, the method can be carried out in other containers such as those described in more detail in U.S. Pat. No. 4,902,624 (Columbus et al), U.S. Pat. No. 5,173,260 (Zander et al) and U.S. Pat. No. 5,229,297 (Schnipelsky et al), all incorporated herein by reference, and any other suitable container which is readily apparent to one skilled in the art. Such test packs are also known as self-contained test devices which have separate compartments for various reagents used in the method of this invention. The compartments are appropriately connected so reagents and assay solutions can be brought into contact with the capture reagent at appropriate times without opening the device.

Detection of amplified products can be accomplished using any known procedure, including Southern blotting techniques, as described in U.S. Pat. No. 4,965,188 (noted above), or by use of labeled probes or primers, as is known in the art.

Alternatively to the embodiments described above, the amplified products can be detected using a labeled oligonucleotide which is complementary to one of the primer extension products.

In the heterogeneous detection systems of this invention, the amplified products are captured on a water-insoluble substrate of some kind, and the other materials in the reaction mixture are removed in a suitable manner, such as by filtration, centrifugation, washing or another separation technique.

Capture probes can be attached to water-insoluble supports using known attachment techniques (including absorption and covalent reactions).

One such technique is described in EP-A-0 439 222 (published Sep. 18, 1991). Other techniques are described, for example, in U.S. Pat. No. 4,713,326 (Dattagupta et al), U.S. Pat. No. 4,914,210 (Levenson et al) and EP-B-0 070 687 (published Jan. 26, 1983). Useful separation means include filtration through membranes such as polyamide microporous membranes commercially available from Pall Corporation.

However, any useful solid support can be used to anchor the capture probe and eventual hybridization product, including microtiter plates, test tubes, beakers, magnetic or polymeric particles, metals, ceramics, and glass wool to name a few. Particularly useful materials are magnetic or polymeric particles having reactive groups useful for covalently attaching the capture probe. Such particles are generally from about 0.001 to about 10 μmeters. Further details about examples of such materials are provided in U.S. Pat. No. 4,997,772 (Sutton et al), U.S. Pat. No. 5,147,777 (Sutton et al), U.S. Pat. No. 5,155,166 (Danielson et al) and U.S. Pat. No. 4,795,698 (Owen et al), all incorporated herein by reference.

The capture probe can be affixed to a flat support such as a polymeric film, membranes, filter papers, or resin-coated or uncoated paper. Capture probe affixed to polymeric particles can also be immobilized on such flat supports in a suitable manner, for example, as dried deposits, or adhered by heat fusion or with adhesives. The capture probe can be affixed, for example, to a flat support in the self-contained test device of this invention. Other details of such materials are provided in EP-A-0 408 738 (published Jan. 23, 1991), WO 92/16659 (published Oct. 1, 1992) and U.S. Pat. No. 5,173,260 (Sutton et al).

The capture probes can be arranged on a suitable support in any configuration, for example rows of round deposits or stripes.

The present invention can also be used in what are known as "homogeneous" amplification procedures in which target nucleic acids are detected without the need for capture reagents. The details of such assays are known in the art, such as EP-A-0 487 218 (published May 27, 1992) and EP-A-0 512 334 (published Nov. 11, 1992).

The amplification reaction composition can be included as one individually packaged component of a test kit useful for various amplification assays. The kit can include other reagents, solutions, equipment and instructions useful in the method of this invention, including capture reagents immobilized on a water-insoluble substrate, wash solutions, lysing solutions, detection reagents and other materials readily apparent to one skilled in the art. In addition, the test kit can include separately packaged polyethyleneimine as described above, one or more anionic phosphate ester surfactants, buffers, strong bases and other reagents needed for either or both amplification and specimen sample preparation. The test kit can also include a test device containing one or more other kit components. This test device is preferably "self-contained" as that term is understood in the art. Other test kits can be assembled that are useful for hybridization assays, for example containing detection capture probes for the target nuclei acid.

The following examples are included to illustrate the practice of this invention, and are not meant to be limiting in any way. All percentages are by weight unless otherwise noted.

MATERIALS AND METHODS FOR EXAMPLES

Recombinant DNA polymerase from *Thermus aquaticus* was prepared using conventional methods.

The following primers and probes were prepared using known starting materials and procedures using a BIOSEARCH™ Model 8700 DNA synthesizer and standard phosphoramidite chemistry, and had the following sequences which are complementary to the major capsid protein region of human cytomegaloviral (hCMV) DNA:

SEQ ID:NO:1

5'-X-CATTCCCACT GACTTTCTGA CGCACGT-3'
SEQ ID:NO:2

5'-X-TGAGG TCGTG GAACT TGATG GCGT-3'
SEQ ID:NO:3

5'-GGTCATCGCC GTAGTAGATG CGTAAGGCCT-Y-3'

In the first two sequences for primers, X represents a biotin moiety attached to the sequence through two tetraethylene glycol spacer units using the teaching of U.S. Pat. No. 4,914,210 (Levenson et al), incorporated herein by reference. All purifications were carried out using a nucleic acid purification column, followed by reversed phase HPLC techniques.

The third sequence was used as a capture probe wherein Y contains two tetraethylene glycol spacers connected by a phosphate linkage, and a 3-amino-1,2-propanediol moiety prepared using the procedures of the Levenson et al patent noted above.

Deoxyribonucleotides (dNTP's) and calf thymus DNA were obtained from Sigma Chemical Co.

The monoclonal antibody specific to the noted DNA polymerase was prepared as described in U.S. Pat. No. 5,338,671 (noted above). Generally, it was prepared from the immune cells of DNA polymerase immunized mice using conventional procedures, such as those described by Milstein et al, *Nature* 256, pp. 495–497, 1975 and hybridoma cell lines (either HB 11126 or 11127 from ATCC), whereby antibody secreting cells of the host animal were isolated from lymphoid tissue (such as the spleen) and fused with SP2/0-Ag14 murine myeloma cells in the presence of polyethylene glycol, diluted into selective media and plated in multiwell tissue culture dishes. About 7–14 days later, the hybridoma cells containing the antibodies were harvested, and purified using conventional techniques.

A streptavidin-peroxidase conjugate solution comprised a commercially available (Zymed Laboratories, Inc.) conjugate of streptavidin and horseradish peroxidase (126 μl/l), 4'-hydroxyacetanilide (10 mmolar), casein (0.5%) and merthiolate (0.5%).

A wash solution (pH 7.4) contained sodium phosphate, monobasic 1-hydrate (25 mmolar), sodium chloride (373 mmolar), (ethylenedinitrilo)tetraacetic acid disodium salt (2.5 mmolar), ethylmercurithiosalicylic acid sodium salt (25 μmolar), and decyl sodium sulfate (38 mmolar).

The dye-providing composition (pH 6.8) contained 4,5-bis(4-dimethylaminophenyl)-2-(4-hydroxy-3-methoxyphenyl)imidazole leuco dye (250 μmolar), poly(vinyl pyrrolidone) (112 mmolar), hydrogen peroxide (0.03%), diethylenetriaminepentaacetic acid (100 μmolar), 3'-chloro-4'-hydroxyacetanilide (5 mmolar) and sodium phosphate, monobasic, 1-hydrate (10 mmolar).

The aqueous dye signal stop solution contained 0.1% sodium azide.

The capture probe reagent was prepared by attaching SEQ ID NO:3 oligonucleotide identified above to particles of poly[styrene-co-3-(p-vinylbenzylthio)-propionic acid] (95:5 weight ratio, 1 μm average diameter) in the following manner. A suspension of the particles in water was washed twice with 2-(N-morpholino)ethanesulfonic acid buffer (0.1 molar, pH 6), and suspended to approximately 10% solids. A sample (3.3 ml) of the washed particles, diluted to 3.33% solids in the buffer (0.1 molar), was mixed with 1-(3-dimethylaminopropyl)-3-ethylcarbodiimide hydrochloride (2.1 ml of 84 mg/ml water) and the appropriate probe (22 μl of 44.44 OD/ml nanopure water). The resulting suspension was heated at 50° C. in a water bath for about two hours with intermittent mixing and centrifuged. The particles were washed three times with tris(hydroxymethyl)aminomethane buffer (0.01 molar, pH 8) containing (ethylenedinitrilo)tetraacetic acid disodium salt (0.001 molar) and resuspended therein to 4% solids.

A PCR reaction mixture comprised: tris(hydroxymethyl)aminomethane hydrochloride buffer (10 mmolar), potassium chloride (50 mmolar), magnesium chloride (10 mmolar), gelatin (100 μg/ml), dATP, dCTP, dGTP and dTTP (1 mmolar of each), glycerol (9.5%), primers (0.4 μmolar of each), DNA polymerase identified above (16 units/100 μl), and a monoclonal antibody specific to DNA polymerase identified above (50:1 molar ratio to DNA polymerase).

SURECELL™ test devices are available from Eastman Kodak Company (Clinical Diagnostics Division), and contain three test wells, each with a mounted LOPRODYNE™ microporous membrane (Pall Corp., 5 μmeter average pore size). The capture probe reagent was disposed and dried on the membranes in the test wells of the test devices.

DEQUEST™ 2006 anionic aminotri(methylene-phosphonic acid)pentasodium salt surfactant was obtained from Monsanto Co.

ZONYL™ FSP anionic fluorinated phosphate ester surfactant was obtained from DuPont.

MONAWET™ B-174 anionic sodium dioctylphosphosuccinate surfactant was obtained from Mona Industries.

RHODAFAC™ L0529 anionic partial sodium salt of an aromatic alkylene oxide phosphate ester surfactant was obtained from Rhone Poulenc.

EMPHOS™ CS413 anionic oxyalkylated alkylphosphate ester surfactant and EMPHOS™ CS141 anionic polyoxyalkylated alkylaryl phosphate ester were obtained from Witco Chemical Co.

Polyethyleneimine was obtained from Bethesda Research Laboratories (also available from BASF Corp.).

Other reagents and materials were obtained either from commercial sources or prepared using readily available starting materials and conventional procedures.

EXAMPLE 1

Capture and Release of DNA

This example illustrates the practice of the present invention to capture and release a nucleic acid using polyethyleneimine and an anionic fluorinated phosphate ester surfactant.

A sample (5 μl) of a 1:10 dilution of 10% polyethyleneimine in distilled water was mixed with a solution (95 μl) of calf thymus DNA (0.5 μg/μl) by vortexing. The resulting mixture was then centrifuged at 14,000 rpm for 5 minutes to form a pellet of the resulting precipitate of DNA and polyethyleneimine complex.

The supernatant was discarded and sodium hydroxide (75 μl, 50 molar) was added to the vessel containing the pellet, followed by vortex mixing. The resulting pH was about 11.

A solution (10 μl, at 0.5%, 0.25% or 0.125% final concentration) of anionic surfactant (see Table I) was added to the high pH mixture, and mixed by vortexing. The resulting solution was then neutralized to a pH of about 8 by adding 15 μl of tris(hydroxymethyl)aminomethane hydrochloride buffer (1 molar).

Release of the nucleic acids was verified using conventional gel electrophoresis. An aliquot (5 μl) of the resulting solution containing nucleic acids, polyethyleneimine and surfactant was mixed with a conventional sample tracking dye in a microcentrifuge tube. A sample (4 μl) was then loaded onto a 0.5% conventional agarose gel prestained with ethidium bromide, and electrophoresis was performed at 120 volts for 30 minutes. Gel bands were visualized under ultraviolet light. The presence of a genomic DNA band that migrated in a similar fashion as the conventional lambda DNA marker indicated that nucleic acids had been released from the polyethyleneimine.

In order to determine if any aspect of the foregoing sample preparation method would inhibit amplification by PCR, human cytomegaloviral (hCMV) DNA was added to each neutralized sample so prepared and subjected to the PCR protocol noted below.

More specifically, an aliquot (20 μl) of each neutralized sample containing the anionic surfactant and released calf thymus DNA was mixed with a solution (10 μl) of hCMV target nucleic acid from the major capsid protein region of the hCMV genome (1:10 dilution of a stock solution containing $1-5 \times 10^5$ copies/μl). A second aliquot (20 μl) of each sample was mixed with a 1:100 dilution of the target nucleic acid.

To each resulting mixture (30 μl) was added the PCR amplification reaction mixture (70 μl) identified above, and amplification carried out for 40 cycles using the following protocol:

1) denaturation at 95° C. for 30 seconds (210 seconds for first cycle), and 2) primer annealing and primer extension at 64° C. for 30 seconds.

After amplification, two methods were used to detect the presence of amplified hCMV DNA:

(a) Gel electrophoresis: An aliquot (10 μl) of each amplified product solution was added to 4 μl of a conventional sample tracking dye. The resulting mixture (10 μl) was loaded onto a 2.5% agarose gel that was pre-stained with ethidium bromide. Electrophoresis was carried out for 1.5 hours at 120 volts. Gel bands were visualized under ultraviolet light.

(b) Dye signal in SURECELL™ test device: A sample (95 μl) of a 1:20 dilution of each amplified product sample was heated at 95° C. for 5 minutes to denature the amplification products, and contacted with the capture reagent which had been dried on the membranes of SURECELL™ test device test wells. The devices were then incubated at 50° C. for 5 minutes and washed at room temperature with the wash solution described above to remove unbound materials.

A solution (100 μl) of streptavidin-conjugated horseradish peroxidase (131 ng/ml) was added to each test well followed by 2 minutes incubation at room temperature. Another wash was performed, followed by the addition of the leuco dye solution (100 μl) described above and an additional two minute incubation at room temperature. Dye development was stopped by addition of the sodium azide solution.

Table I below shows the gel electrophoretic and dye color score results for several specimens using various amounts of several anionic surfactants. It is apparent that ZONYL FSP™ anionic surfactant provided the strongest signals and did not inhibit PCR of the target nucleic acid. The dye color scores were graded on a density gradient of from 0 to 10 (highest density). The electrophoretic gel scores were negative (−), slightly positive (w+), clearly positive (+) and very positive (++).

Several amplifications were also carried out by omitting the use of polyethyleneimine or surfactant. The results of these assays are the last four lines of Table I. The last two lines show the results where no surfactant or polyethyleneimine was used. While the signals were high, it must be understood that these data are from "clean" samples having no interferents or inhibitors. In clinical samples, inhibitors and interferents would likely reduce those signals or prevent amplification altogether. It is the purpose of this invention, therefore, to provide a means for separating target nucleic acids from such adverse materials, and the results in Table I demonstrate that the use of polyethyleneimine and a fluorinated surfactant according to this invention accomplishes this purpose.

Figure 1:
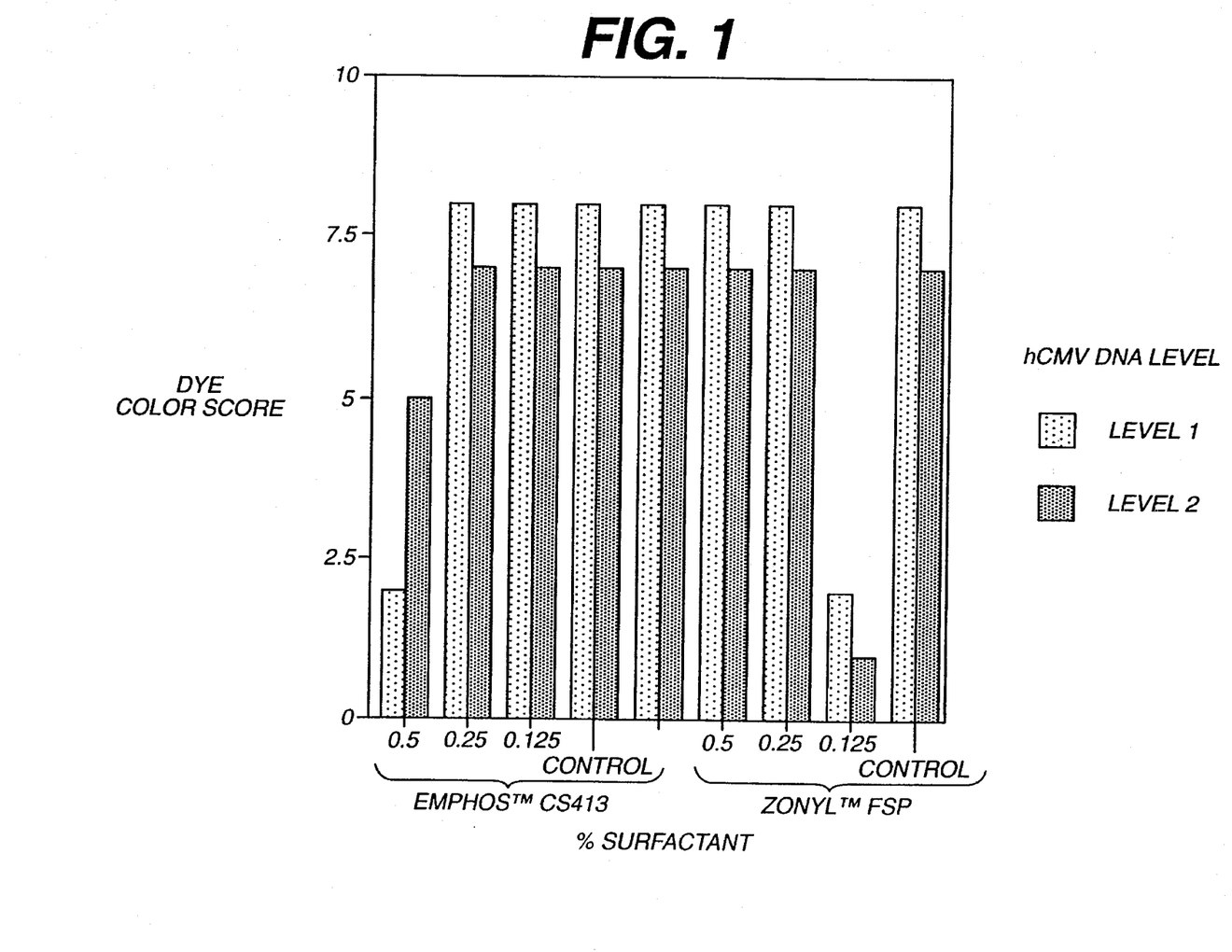
FIG. 1 illustrate some of the data obtained in Example 1 below is bar graphical form.

FIG. 1 illustrates the dye color score data in bar graphical form for the various levels of two preferred surfactants, EMPHOS™ CS413 and ZONYL™ FSP anionic surfactants, respectively. The hCMV DNA levels were the 1:10 (Level 1) and 1:100 (Level 2). The Control data were obtained in the absence of both surfactants.

was then added to the high pH mixture with mixing. Tris(hydroxymethyl)aminomethane hydrochloride (15 µl, 1 molar, pH 7.5) was then added to neutralize the solution for amplification.

TABLE I

| Surfactant | Final Weight % | hCMV DNA | Dye Color Score | Gel Score |
|---|---|---|---|---|
| DEQUEST ™ 2006 | 0.5 | 1:10 | 0 | — |
| DEQUEST ™ 2006 | 0.25 | 1:10 | 0 | — |
| DEQUEST ™ 2006 | 0.125 | 1:10 | 0 | — |
| DEQUEST ™ 2006 | 0.5 | 1:100 | 0 | — |
| DEQUEST ™ 2006 | 0.25 | 1:100 | 0 | — |
| DEQUEST ™ 2006 | 0.125 | 1:100 | 0 | — |
| MONAWET ™ B-124 | 0.5 | 1:10 | 0 | — |
| MONAWET ™ B-124 | 0.25 | 1:10 | 0 | — |
| MONAWET ™ B-124 | 0.125 | 1:10 | 0 | — |
| MONAWET ™ B-124 | 0.5 | 1:100 | 0 | — |
| MONAWET ™ B-124 | 0.25 | 1:100 | 0 | — |
| MONAWET ™ B-124 | 0.125 | 1:100 | 0 | — |
| RHODAFAC ™ LO529 | 0.5 | 1:10 | 0 | — |
| RHODAFAC ™ LO529 | 0.25 | 1:10 | 0 | — |
| RHODAFAC ™ LO529 | 0.125 | 1:10 | 0 | — |
| RHODAFAC ™ LO529 | 0.5 | 1:100 | 0 | — |
| RHODAFAC ™ LO529 | 0.25 | 1:100 | 0 | — |
| RHODAFAC ™ LO529 | 0.125 | 1:100 | 0 | — |
| EMPHOS ™ CS413 | 0.5 | 1:10 | 2 | — |
| EMPHOS ™ CS413 | 0.25 | 1:10 | 8 | + |
| EMPHOS ™ CS413 | 0.125 | 1:10 | 8 | + |
| EMPHOS ™ CS413 | 0.5 | 1:100 | 5 | — |
| EMPHOS ™ CS413 | 0.25 | 1:100 | 7 | + |
| EMPHOS ™ CS413 | 0.125 | 1:100 | 7 | + |
| EMPHOS ™ CS141 | 0.5 | 1:10 | 0 | — |
| EMPHOS ™ CS141 | 0.25 | 1:10 | 0 | — |
| EMPHOS ™ CS141 | 0.125 | 1:10 | 0 | — |
| EMPHOS ™ CS141 | 0.5 | 1:100 | 0 | — |
| EMPHOS ™ CS141 | 0.25 | 1:100 | 0 | — |
| EMPHOS ™ CS141 | 0.125 | 1:100 | 6 | w+ |
| ZONYL ™ FSP | 0.5 | 1:10 | 8 | ++ |
| ZONYL ™ FSP | 0.25 | 1:10 | 8 | ++ |
| ZONYL ™ FSP | 0.125 | 1:10 | 2 | — |
| ZONYL ™ FSP | 0.5 | 1:100 | 7 | + |
| ZONYL ™ FSP | 0.25 | 1:100 | 7 | + |
| ZONYL ™ FSP | 0.125 | 1:100 | 1 | — |
| None | — | 1:10 | 0 | — |
| None | — | 1:100 | 0 | — |
| None* | — | 1:10 | 8 | ++ |
| None* | — | 1:100 | 7 | + |

*: No capture of calf thymus DNA with polyethyleneimine.

EXAMPLE 2

Sample Preparation and Amplification of Human Cytomegaloviral DNA

This example demonstrates the practice of the present invention to capture and release hCMV DNA for amplification in the presence of background DNA, i.e. calf thymus DNA.

Samples (10 µl) of hCMV dilutions were mixed with calf thymus DNA (95 µl, 0.5 µg/µl), followed by mixing with a 1:10 dilution of polyethyleneimine (10%) to form a precipitate of polyethyleneimine and the nucleic acids.

This precipitate was separated from the solution by centrifugation at 14,000 rpm for 5 minutes. The supernatant was discarded, and the pellet was added to sodium hydroxide (75 µl, 50 molar) with mixing.

A solution (10 µl) of ZONYL™ FSP anionic surfactant (1.5%, 1.0%, 0.5%, 0.25% or 0.125% final concentration)

An aliquot (20 µl) of each sample treated as noted above, were added to the PCR reagent mixture (80 µl) containing the hCMV primers identified above, and 40 cycles of PCR were carried out using the protocol described above in Example 1.

Detection of amplified products was achieved using both gel electrophoresis and dye color signal generation as described above in Example 1. Table II below shows the results for two replicates for each sample, and FIG. 2 shows the color score data in a bar graph.

PCR was inhibited for all levels of target hCMV DNA when 1.5% surfactant (final concentration) was used. Moreover, the lower amounts of 0.125% and 0.25% were not useful because high background was observed. Optimum results were achieved using 0.5% or 1.0% surfactant, and the lower amount was more useful at the lower concentrations of target nucleic acid. PCR was not observed in Control assays where no surfactant was used. Signal was obtained where no polyethyleneimine or surfactant were used, but these data were obtained with "clean" samples having no interferents or inhibitors which are typically present in clinical specimens.

Figure 2:
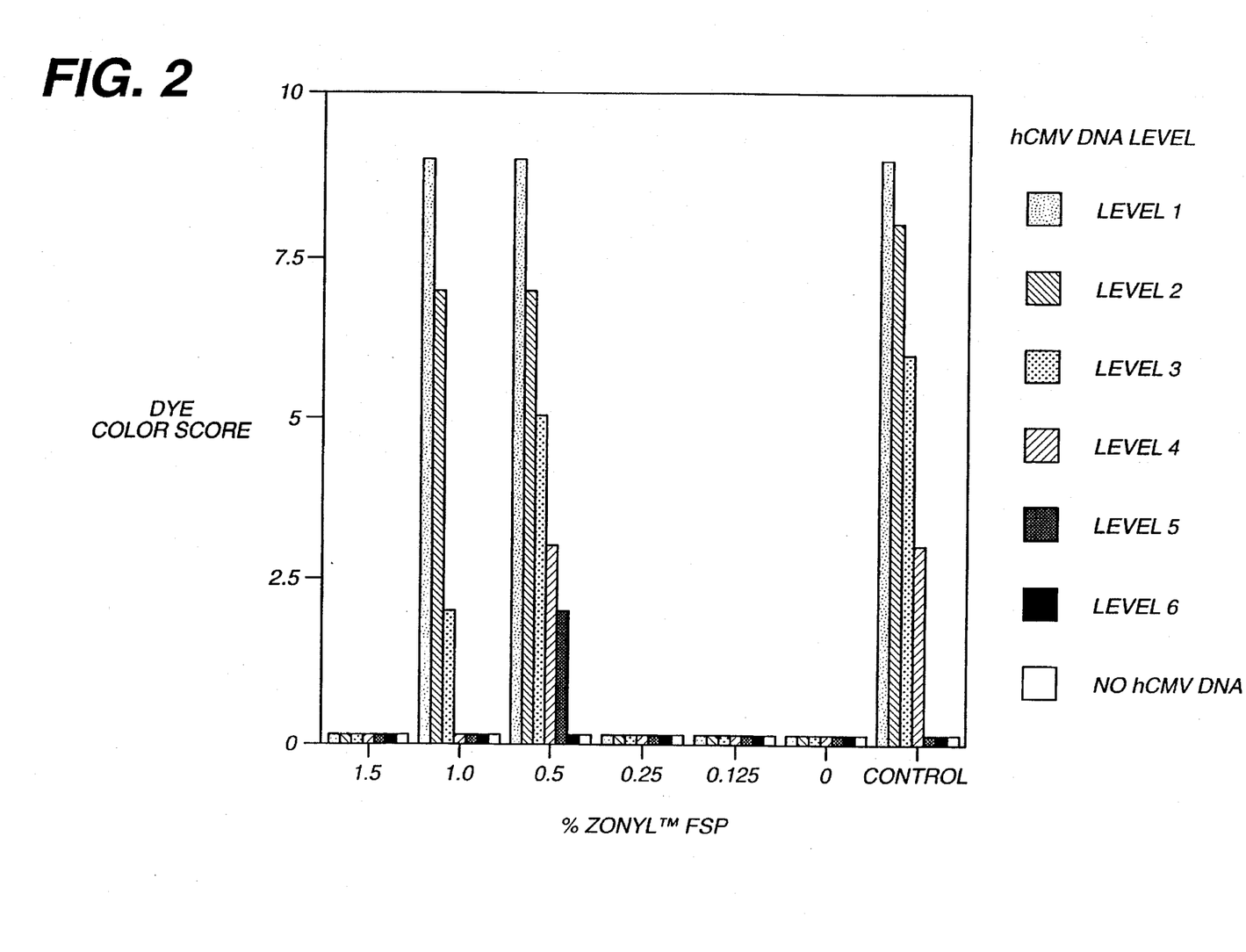
FIG. 2 illustrates the data obtained in Example 2 below in bar graphical form.

In FIG. 2, the dye color scores are shown at various target nucleic acid levels for the preferred surfactant, ZONYL™ FSP anionic surfactant. No polyethyleneimine or surfactant was used in the Control assay. The hCMV concentration levels identified in FIG. 2 and in Table II below were as follows:
Level 1: 1:10 dilution of stock
Level 2: 1:100 dilution of stock
Level 3: 1:1,000 dilution of stock
Level 4: 1:10,000 dilution of stock
Level 5: 1:100,000 dilution of stock
Level 6: 1:1,000,000 dilution of stock
Level 7: No hCMV DNA

TABLE II

| Final Surfactant Level | Poly-ethylene-imine (?) | hCMV DNA Level | Dye Color Score | Gel Score |
|---|---|---|---|---|
| 1.5% | yes | 1 | 0/0 | −/− |
| 1.5% | yes | 2 | 0/0 | −/− |
| 1.5% | yes | 3 | 0/0 | −/− |
| 1.5% | yes | 4 | 0/0 | −/− |
| 1.5% | yes | 5 | 0/0 | −/− |
| 1.5% | yes | 6 | 0/0 | −/− |
| 1.5% | yes | 7 | 0/0 | −/− |
| 1.0% | yes | 1 | 9/9 | ++/++ |
| 1.0% | yes | 2 | 7/7 | w+/w+ |
| 1.0% | yes | 3 | 2/2 | −/− |
| 1.0% | yes | 4 | 0/0 | −/− |
| 1.0% | yes | 5 | 0/0 | −/− |
| 1.0% | yes | 6 | 0/0 | −/− |
| 1.0% | yes | 7 | 0/0 | −/− |
| 0.5% | yes | 1 | 9/9 | +/+ |
| 0.5% | yes | 2 | 7/7 | w+/w+ |
| 0.5% | yes | 3 | 5/5 | −/− |
| 0.5% | yes | 4 | 3/3 | −/− |
| 0.5% | yes | 5 | 2/2 | −/− |
| 0.5% | yes | 6 | 0/0 | −/− |
| 0.5% | yes | 7 | 0/0 | −/− |
| 0.25% | yes | 1 | 0/0 | −/− |
| 0.25% | yes | 2 | 0/0 | −/− |
| 0.25% | yes | 3 | 0/0 | −/− |
| 0.25% | yes | 4 | 0/0 | −/− |
| 0.25% | yes | 5 | 0/0 | −/− |
| 0.25% | yes | 6 | 0/0 | −/− |
| 0.25% | yes | 7 | 0/0 | −/− |
| 0.125% | yes | 1 | 0/0 | −/− |
| 0.125% | yes | 2 | 0/0 | −/− |
| 0.125% | yes | 3 | 0/0 | −/− |
| 0.125% | yes | 4 | 0/0 | −/− |
| 0.125 | yes | 5 | 0/0 | −/− |
| 0.125 | yes | 6 | 0/0 | −/− |
| 0.125 | yes | 7 | 0/0 | −/− |
| 0 | yes | 1 | 0/0 | −/− |
| 0 | yes | 2 | 0/0 | −/− |
| 0 | yes | 3 | 0/0 | −/− |
| 0 | yes | 4 | 0/0 | −/− |
| 0 | yes | 5 | 0/0 | −/− |
| 0 | yes | 6 | 0/0 | −/− |
| 0 | yes | 7 | 0/0 | −/− |
| 0 | no | 1 | 9/9 | ++/++ |
| 0 | no | 2 | 8/8 | +/+ |
| 0 | no | 3 | 6/6 | −/− |
| 0 | no | 4 | 3/3 | −/− |
| 0 | no | 5 | 0/0 | −/− |
| 0 | no | 6 | 0/0 | −/− |

EXAMPLE 3

Capture and Release of Target hCMV DNA and Amplification in Absence of Background DNA This example was carried out exactly as described in Example 2 except that the hCMV DNA dilution samples were mixed with a buffer solution (95 μl) containing tris(hydroxymethyl)aminomethane hydrochloride (10 mmolar, pH 8) and TWEEN™ 20 nonionic surfactant (0.5%) instead of the calf thymus DNA solution.

Figure 3:
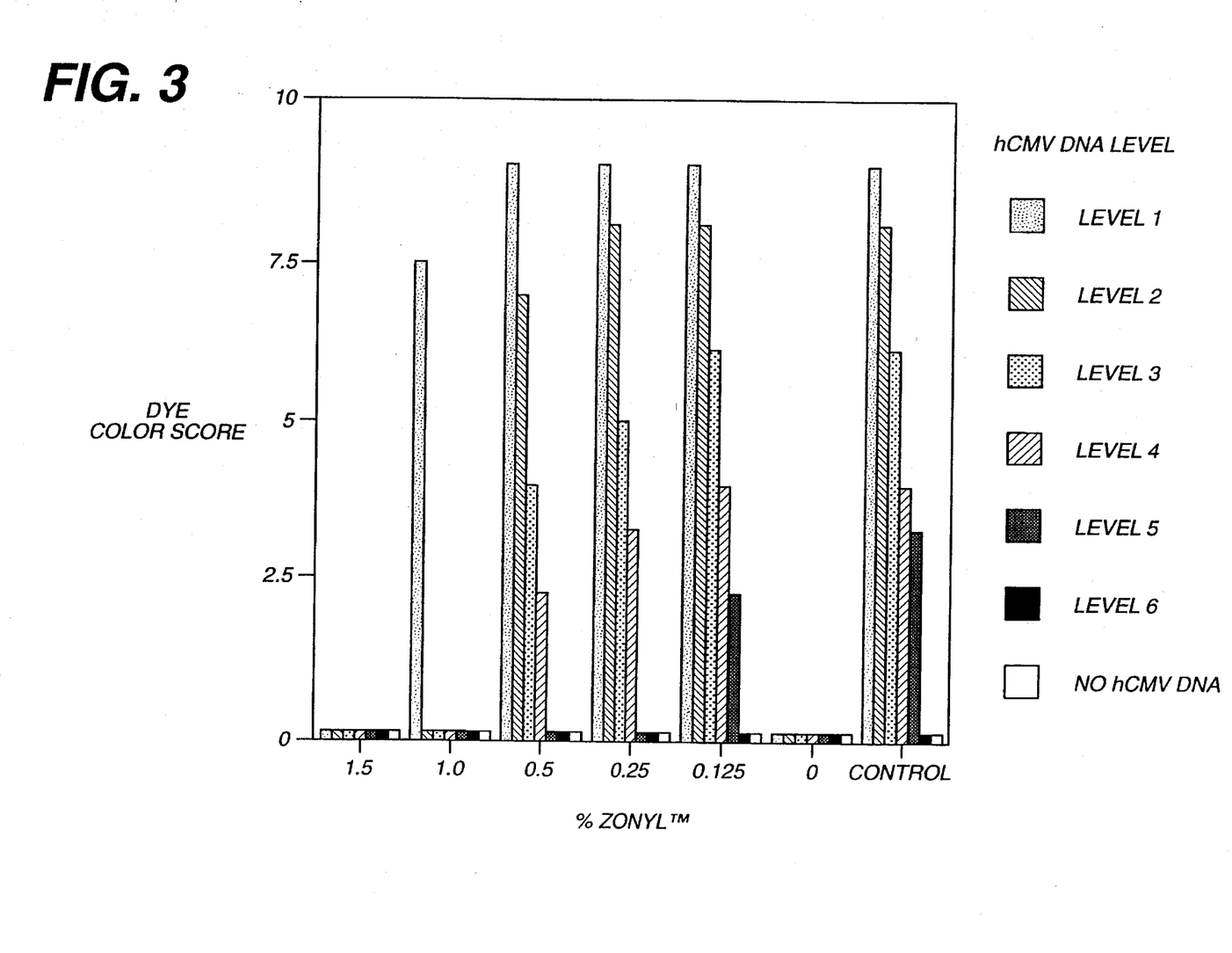
FIG. 3 illustrates the data obtained in Example 3 below in bar graphical form.

Amplification and detection of the captured and release target hCMV DNA was carried out as described above. The results are shown in FIG. 3 and in Table III below. The target nucleic acid levels identified therein are the same as described in Example 2 above.

The results indicate that the use of 1.5% surfactant inhibited PCR, as did the absence of surfactant. There was some level of background in most assays, but the level was generally acceptable.

TABLE III

| Final Surfactant Level | Poly-ethylene-imine (?) | hCMV DNA Level | Dye Color Score | Gel Score |
|---|---|---|---|---|
| 1.5% | yes | 1 | 0/0 | −/− |
| 1.5% | yes | 2 | 0/0 | −/− |
| 1.5% | yes | 3 | 0/0 | −/− |
| 1.5% | yes | 4 | 0/0 | −/− |
| 1.5% | yes | 5 | 0/0 | −/− |
| 1.5% | yes | 6 | 0/0 | −/− |
| 1.5% | yes | 7 | 0/0 | −/− |
| 1.0% | yes | 1 | 7/8 | w+/w+ |
| 1.0% | yes | 2 | 0/0 | −/− |
| 1.0% | yes | 3 | 0/0 | −/− |
| 1.0% | yes | 4 | 0/0 | −/− |
| 1.0% | yes | 5 | 0/0 | −/− |
| 1.0% | yes | 6 | 0/0 | −/− |
| 1.0% | yes | 7 | 0/0 | −/− |
| 0.5% | yes | 1 | 9/9 | ++/++ |
| 0.5% | yes | 2 | 7/7 | w+/w+ |
| 0.5% | yes | 3 | 4/4 | −/− |
| 0.5% | yes | 4 | 2/2 | −/− |
| 0.5% | yes | 5 | 0/0 | −/− |
| 0.5% | yes | 6 | 0/0 | −/− |
| 0.5% | yes | 7 | 0/0 | −/− |
| 0.25% | yes | 1 | 9/9 | ++/++ |
| 0.25% | yes | 2 | 8/8 | +/+ |
| 0.25% | yes | 3 | 5/5 | −/− |
| 0.25% | yes | 4 | 3/3 | −/− |
| 0.25% | yes | 5 | 0/0 | −/− |
| 0.25% | yes | 6 | 0/0 | −/− |
| 0.25% | yes | 7 | 0/0 | −/− |
| 0.125% | yes | 1 | 9/9 | ++/++ |
| 0.125% | yes | 2 | 8/8 | +/+ |
| 0.125% | yes | 3 | 6/6 | −/− |
| 0.125% | yes | 4 | 4/4 | −/− |
| 0.125% | yes | 5 | 2/2 | −/− |
| 0.125% | yes | 6 | 0/0 | −/− |
| 0.125% | yes | 7 | 0/0 | −/− |
| 0 | yes | 1 | 0/0 | −/− |
| 0 | yes | 2 | 0/0 | −/− |
| 0 | yes | 3 | 0/0 | −/− |
| 0 | yes | 4 | 0/0 | −/− |
| 0 | yes | 5 | 0/0 | −/− |
| 0 | yes | 6 | 0/0 | −/− |
| 0 | yes | 7 | 0/0 | −/− |
| 0 | no | 1 | 9/9 | ++/++ |
| 0 | no | 2 | 8/8 | +/+ |
| 0 | no | 3 | 6/6 | +/+ |
| 0 | no | 4 | 4/4 | −/− |
| 0 | no | 5 | 3/3 | −/− |
| 0 | no | 6 | 0/0 | −/− |

EXAMPLE 4

Capture Release and Amplification of hCMV DNA in the Presence of Various Amounts of Background DNA This example illustrates the practice of this invention in the presence of various amounts of background calf thymus DNA in the tested sample. The procedures were carried out exactly as described in Example 2 above except that the target nucleic acid dilutions were mixed with 95 µl of solution containing various amounts of calf thymus DNA (55 µg, 25 µg, 10 µg or 5 µg final amounts).

Amplification and detection were accomplished as described in Example 2 (except electrophoretic gels were not used). The dye color score results are provided in Table IV below. The results indicated that 0.5% final surfactant concentration was sufficient to keep the nucleic acids solubilized so optimum amplification could be carried out for the entire range of background DNA present in the samples. Results using the lower amounts of surfactant indicated high background, but the conditions might be adjusted or a different surfactant used to minimize this effect.

TABLE IV

| Surfactant Level | Background DNA Level (µg) | hCMV Level (Dilution) | Dye Color Score |
|---|---|---|---|
| 0.5% | 55 | 1 | 9 |
| 0.25% | 55 | 1 | 0 |
| 0.125% | 55 | 1 | 0 |
| 0.5% | 55 | 3 | 6 |
| 0.25% | 55 | 3 | 0 |
| 0.125% | 55 | 3 | 0 |
| 0.5% | 55 | 4 | 4 |
| 0.25% | 55 | 4 | 0 |
| 0.125% | 55 | 4 | 0 |
| 0.5% | 25 | 1 | 9 |
| 0.25% | 25 | 1 | 8 |
| 0.125% | 25 | 1 | 8 |
| 0.5% | 25 | 3 | 6 |
| 0.25% | 25 | 3 | 5 |
| 0.125% | 25 | 3 | 5 |
| 0.5% | 25 | 4 | 4 |
| 0.25% | 25 | 4 | 4 |
| 0.125% | 25 | 4 | 3 |
| 0.5% | 10 | 1 | 9 |
| 0.25% | 10 | 1 | 9 |
| 0.125% | 10 | 1 | 9 |
| 0.5% | 10 | 3 | 6 |
| 0.25% | 10 | 3 | 6 |
| 0.125% | 10 | 3 | 6 |
| 0.5% | 10 | 4 | 4 |
| 0.25% | 10 | 4 | 4 |
| 0.125% | 10 | 4 | 4 |
| 0.5% | 5 | 1 | 9 |
| 0.25% | 5 | 1 | 9 |
| 0.125% | 5 | 1 | 9 |
| 0.5% | 5 | 3 | 6 |
| 0.25% | 5 | 3 | 6 |
| 0.125% | 5 | 3 | 6 |
| 0.5% | 5 | 4 | 4 |
| 0.25% | 5 | 4 | 4 |
| 0.125% | 5 | 4 | 4 |
| 0.5% | 0 | 1 | 9 |
| 0.25% | 0 | 1 | 9 |
| 0.125% | 0 | 1 | 9 |
| 0.5% | 0 | 3 | 6 |
| 0.25% | 0 | 3 | 6 |
| 0.125% | 0 | 3 | 6 |
| 0.5% | 0 | 4 | 4 |
| 0.25% | 0 | 4 | 4 |
| 0.125% | 0 | 4 | 4 |
| 0.5% | 55 | 1 | 9 |
| 0.25% | 55 | 3 | 7 |
| 0.125% | 55 | 4 | 5 |

EXAMPLE 5

Capture and Release of Target hCMV DNA In Patient Samples and Amplification

This example demonstrates the practice of the present invention using 9 hCMV culture positive and 3 hCMV culture negative urine specimens obtained from a medical center. It also compares the present invention with a commonly used sample preparatory method, that is, heating the sample to 100° C. for 10 minutes in the presence of a nonionic surfactant.

Two aliquots (150 µl each) of each urine specimen were mixed with a buffer solution (150 µl) containing TWEEN™ 20 nonionic surfactant (0.5%) in tris(hydroxymethyl)aminomethane hydrochloride buffer (10 mmolar, pH 8).

The mixtures were each boiled for 10 minutes. To one set of specimens, a 1:10 dilution of 10% polyethyleneimine solution was added and mixed, forming a precipitate of nucleic acids and polyethyleneimine. The resulting suspensions were centrifuged at 14,000 rpm for 5 minutes. The supernatants were discarded, and sodium hydroxide (75 µl, 50 molar) was added to each pellet followed by mixing. A solution (10 µl) of ZONYL™ FSP anionic surfactant (0.5%, final concentration) was added to the high pH suspensions, followed by vortexing. To neutralize the suspensions, tris(hydroxymethyl)-aminomethane (15 µl, 1 molar, pH 7.5) was added.

The second set of specimens received no further treatment.

An aliquot (20 µl) of each solution (for both sets of treated specimens) was added to the PCR reaction mixture (80 µl) described above containing the noted hCMV DNA primers. PCR was carried out for 40 cycles as described in Example 1, and any amplified products were detected by generating a dye color signal (score) as described above.

Figure 4:
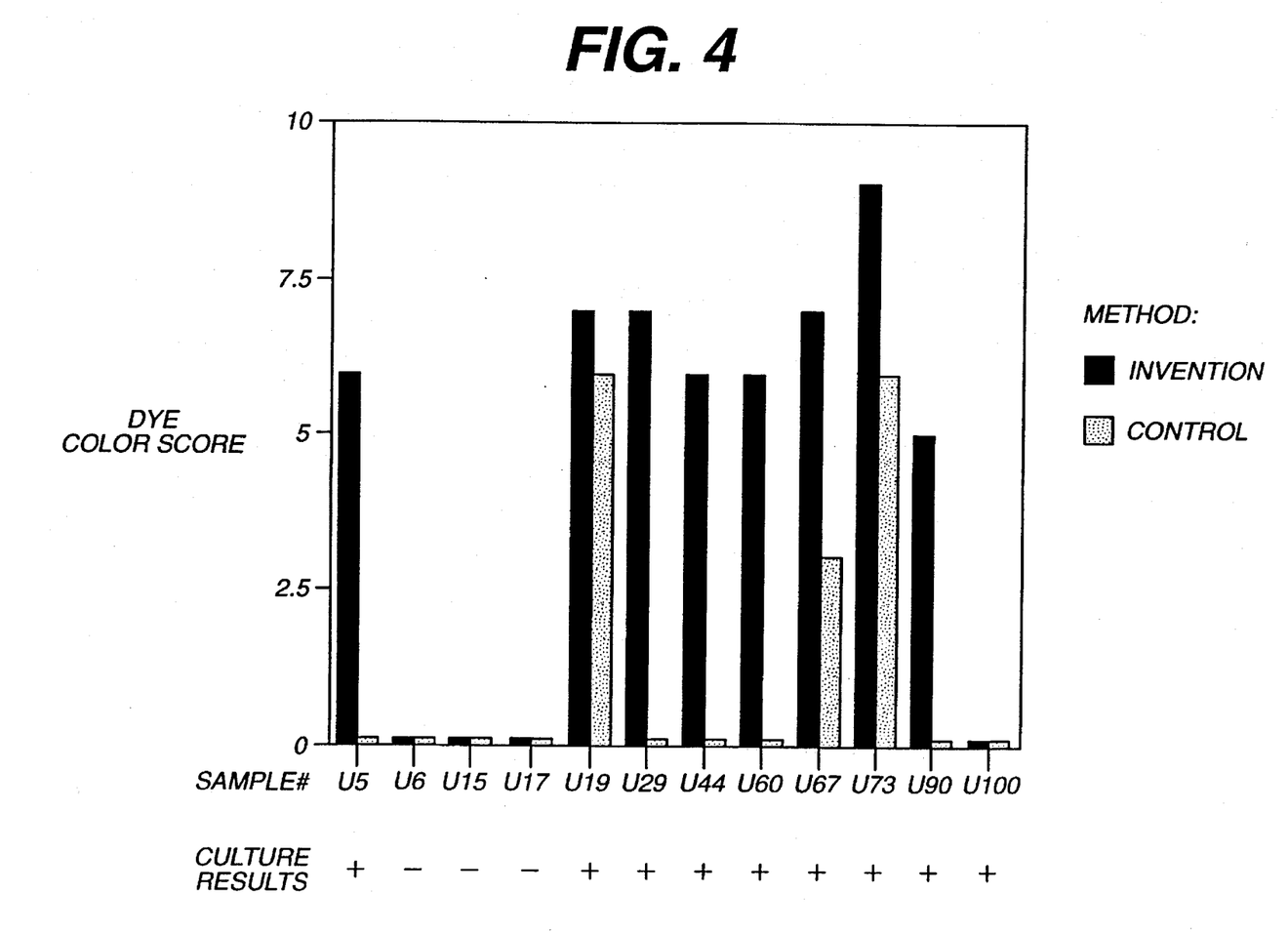
FIG. 4 illustrates data obtained in Example 5 below in bar graphical form.

FIG. 4 and Table V below show the results of both methods, compared with culture results. It is apparent that, in this example, this invention demonstrated a sensitivity of 89% (8 out of 9 culture positive specimens) and a specificity of 100% (3 out of 3 culture negative specimens) when compared with culture results. The control sample preparatory method (heating with nonionic surfactant) displayed a sensitivity of 33% (3 out of 9 culture positive specimens) and a specificity of 100% (3 out of 3 culture negative specimens) when compared with the culture results.

TABLE V

| | URINE SAMPLES | | |
|---|---|---|---|
| Clinical Sample # | Dye Color Score: Invention | Dye Color Score: Control | Culture Results |
| U5 | 6 | 0 | + |
| U6 | 0 | 0 | − |
| U15 | 0 | 0 | − |
| U17 | 0 | 0 | − |
| U19 | 7 | 6 | + |
| U29 | 7 | 0 | + |
| U44 | 6 | 0 | + |
| U60 | 6 | 0 | + |
| U67 | 7 | 3 | + |
| U73 | 9 | 6 | + |
| U90 | 5 | 0 | + |
| U100 | 0 | 0 | + |

This example demonstrates the advantage of removing target nucleic acids from inhibitors which may be present in clinical specimens. Other methods used in the art can accomplish the same result, but in a more tedious, time-consuming and environmentally unsafe manner.

The invention has been described in detail with particular reference to preferred embodiments thereof, but it will be understood that variations and modifications can be effected within the spirit and scope of the invention.

We claim:

1. A method for providing a nucleic acid from a lysate comprising the steps of:
   A) contacting a lysate suspected of containing a nucleic acid with polyethyleneimine in an amount sufficient to form a water-insoluble precipitate of polyethyleneimine with all nucleic acids present in said lysate,
   B) separating said water-insoluble precipitate from said lysate,
   C) contacting said separated water-insoluble precipitate with a strong base to release said nucleic acids from the polyethyleneimine,
   D) simultaneously with or subsequently to step C), contacting said nucleic acids with an anionic phosphate ester surfactant selected from the group consisting of nonaromatic, fluorinated phosphate ester surfactants and nonaromatic, nonfluorinated, oxyalkylatedalkyl phosphate ester surfactants to keep said released nucleic acids in solution, and
   E) adjusting the pH of the solution containing said released nucleic acids to from about 6 to about 9.

2. The method of claim 1 wherein said strong base is sodium hydroxide, potassium hydroxide, lithium hydroxide or ammonium hydroxide.

3. The method of claim 1 wherein said polyethyleneimine is used in step A) in an amount of from about 0.005 to about 1 weight %.

4. The method of claim 1 wherein said lysate is obtained by heating a specimen sample in a solution containing a nonionic surfactant.

5. The method of claim 1 wherein said anionic phosphate ester surfactant is used in step D) in an amount of from about 0.05 to about 1.5 weight %.

6. The method of claim 1 wherein said anionic phosphate ester surfactant has the structure wherein M is an alkali metal or ammonium cation.

7. The method of claim 1 carried out within about 15 minutes.

8. A method for the amplification and detection of a target nucleic acid comprising:
   I) providing a target nucleic acid from a lysate using the steps of:
      A) contacting a lysate suspected of containing a nucleic acid with polyethyleneimine in an amount sufficient to form a water-insoluble precipitate of polyethyleneimine with all nucleic acids present in said lysate including a target nucleic acid,
      B) separating said water-insoluble precipitate from said lysate,
      C) contacting said separated water-insoluble precipitate with a strong base to release said nucleic acids from the polyethyleneimine,
      D) simultaneously with or subsequently to step C), contacting said nucleic acids with an anionic phosphate ester surfactant selected from the group consisting of nonaromatic, fluorinated phosphate ester surfactants and nonaromatic, nonfluorinated, oxyalkylatedalkyl phosphate ester surfactants to keep said released nucleic acids in solution, and
      E) adjusting the pH of the solution containing said released nucleic acids to from about 6 to about 9,
   II) amplifying a target nucleic acid among said released nucleic acids, and
   III) detecting said amplified target nucleic acid.

9. The method of claim 8 wherein said amplifying is a polymerase chain reaction catalyzed by a thermostable DNA polymerase and using at least one labeled primer.

10. The method of claim 9 wherein said labeled primer is labeled with biotin, and the resulting amplified biotinylated target nucleic acid is detected by its reaction with a conjugate of avidin and an enzyme.

11. The method of claim 8 wherein:
    said strong base is sodium hydroxide, potassium hydroxide, lithium hydroxide or ammonium hydroxide,
    said polyethyleneimine is used in step A) in an amount of from about 0.005 to about 1 weight %, and
    said anionic phosphate ester surfactant is used in step D) in an amount of from about 0.05 to about 1.5 weight %.

12. The method of claim 11 wherein said strong base is sodium hydroxide, said polyethyleneimine is used in step A) in an amount of from about 0.01 to about 1 weight percent, and said anionic phosphate ester surfactant is used in step D) subsequently to step C) in an amount of from about 0.1 to about 1.5 weight percent and has the structure:

wherein M is an alkali metal or ammonium cation.

13. The method of claim 8 for the amplification and detection of a target nucleic acid associated with HIV1, HIV2, proviral HIV1, proviral HIV2, cytomegalovirus, *Mycobacterium spp.*, human papilloma virus, hepatitis viruses or a human genetic disease using primers specific to and hybridizable with the strands of said target nucleic acid.

14. A test kit for amplification of a target nucleic acid comprising, separately packaged:
    a) an amplification reaction mixture comprising one or more amplification reagents,
    b) polyethyleneimine, and
    c) an anionic phosphate ester surfactant selected from the group consisting of nonaromatic, fluorinated phosphate ester surfactants and nonaromatic, nonfluorinated oxyalkylatedalkyl phosphate ester surfactants.

15. The test kit of claim 14 wherein said amplification reaction mixture comprises a set of primers, at least one of which is labeled, a plurality of dNTP's and a thermostable DNA polymerase.

16. The test kit of claim 14 comprising a test device containing one of more kit components.

17. A method for the detection of a target nucleic acid comprising:
    I) providing a target nucleic acid from a lysate using the steps of:
       A) contacting a lysate suspected of containing a nucleic acid with polyethyleneimine in an amount sufficient to form a water-insoluble precipitate of polyethyleneimine with all nucleic acids present in said lysate including a target nucleic acid, B) separating said water-insoluble precipitate from said lysate C) contacting said water-insoluble precipitate with a strong base to release said nucleic acids from the polyethylenemine, D) simultaneously with or subsequently to step C), contacting said nucleic acids with an anionic phosphate ester surfactant selected from the group consisting of nonaromatic, fluorinated phosphate ester surfactants and nonaromatic, nonflourinated, oxyalklatedalkyl phosphate ester surfactants to keep said released nucleic acids in solution, and E) adjusting the ph of the solution containing said released nucleic acids to from about 6 to about 9, and II) detecting a target nucleic acid among said released nucleic acids in a hybridization assay.

18. A method for providing a nucleic acid from a lysate comprising the steps of:

A) contacting a lysate suspected of containing a nucleic acid with polyethyleneimine in an amount sufficient to form a water-insoluble precipitate of polyethyleneimine with all nucleic acids present in said lysate, B) separating said water-insoluble precipitate from said lysate, C) contacting said separated water-insoluble precipitate with a strong base to release said nucleic acids from the polyethyleneimine, and D) simultaneously with or subsequently to step C), contacting said nucleic acids with an anionic phosphate ester surfactant selected from the group consisting of nonaromatic, fluorinated phosphate ester surfactants and nonaromatic, nonfluorinated, oxyalkylatedalkyl phosphate ester surfactants to keep said released nucleic acids in solution.

* * * * *